United States Patent
Saoji et al.

(10) Patent No.: US 9,533,145 B2
(45) Date of Patent: Jan. 3, 2017

(54) SYSTEMS AND METHODS FOR MAXIMIZING LOUDNESS SENSATION IN A COCHLEAR IMPLANT PATIENT

(71) Applicant: ADVANCED BIONICS AG, Staefa (CH)

(72) Inventors: Aniket Saoji, Newhall, CA (US); Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/899,555

(22) PCT Filed: Jun. 25, 2013

(86) PCT No.: PCT/US2013/047717
§ 371 (c)(1),
(2) Date: Dec. 17, 2015

(87) PCT Pub. No.: WO2014/209287
PCT Pub. Date: Dec. 31, 2014

(65) Prior Publication Data
US 2016/0144177 A1    May 26, 2016

(51) Int. Cl.
*A61N 1/36* (2006.01)
*A61N 1/05* (2006.01)

(52) U.S. Cl.
CPC ......... *A61N 1/36032* (2013.01); *A61N 1/0541* (2013.01); *A61N 1/36146* (2013.01); *A61N 1/36175* (2013.01)

(58) Field of Classification Search
CPC .............. A61N 1/0541; A61N 1/36032; A61N 1/36146; A61N 1/3615; A61N 1/36153; A61N 1/36157; A61N 1/36167; A61N 1/36171; A61N 1/36175; A61N 1/36178
See application file for complete search history.

(56) References Cited

U.S. PATENT DOCUMENTS 6,195,585 B1 * 2/2001 Karunasiri ......... A61N 1/36032
                                                   607/57
6,219,580 B1    4/2001 Faltys et al.
(Continued)

FOREIGN PATENT DOCUMENTS

WO    WO 2013/082185    6/2013

OTHER PUBLICATIONS

International Search Report and Written Opinion received in International Application No. PCT/US13/047717, dated Nov. 4, 2013.

*Primary Examiner* — Eugene T Wu
(74) *Attorney, Agent, or Firm* — ALG Intellectual Property, LLC (57) ABSTRACT

An exemplary system includes a processing facility configured to process an audio signal presented to a cochlear implant patient and a control facility configured to direct a cochlear implant to apply electrical stimulation representative of the audio signal to the cochlear implant patient by 1) directing the cochlear implant to concurrently apply a first biphasic stimulation pulse by way of a first electrode and a second biphasic stimulation pulse by way of a second electrode during a first time slot, and 2) directing the cochlear implant to concurrently apply a third biphasic stimulation pulse by way of the second electrode and a fourth biphasic stimulation pulse by way of a third electrode during a second time slot that immediately follows the first time slot. The third and fourth biphasic stimulation pulses are flipped in phase compared to the first and second biphasic stimulation pulses.

20 Claims, 8 Drawing Sheets

(56) References Cited

U.S. PATENT DOCUMENTS

| | | | |
|---|---|---|---|
| 2009/0125081 A1* | 5/2009 | Spitzer | A61B 5/04001 607/55 |
| 2010/0069996 A1* | 3/2010 | Strahl | A61B 5/04001 607/55 |
| 2012/0130449 A1* | 5/2012 | Carlyon | A61N 1/36032 607/57 |
| 2012/0209351 A1 | 8/2012 | Meister et al. | |
| 2014/0336725 A1* | 11/2014 | Nogueira | A61N 1/0541 607/57 |
| 2015/0018699 A1* | 1/2015 | Zeng | A61B 5/04001 600/509 |

* cited by examiner

SYSTEMS AND METHODS FOR MAXIMIZING LOUDNESS SENSATION IN A COCHLEAR IMPLANT PATIENT

BACKGROUND INFORMATION

It is often desirable to minimize the amount of current needed to achieve comfortable loudness sensation in a cochlear implant patient. For example, by minimizing the amount of current needed to achieve comfortable loudness sensation in a cochlear implant patient, the size of a sound processor included in a cochlear implant system (i.e., the size of a battery module included in the sound processor) may be minimized.

One way to reduce the amount of current utilized by a cochlear implant system is to reduce the compliance voltage associated with a cochlear implant included in the cochlear implant system (i.e., the voltage maintained by the cochlear implant that governs a maximum amplitude of stimulation current that can be delivered by the cochlear implant). Unfortunately, loudness sensation is determined by the amount of charge delivered to individual electrodes or channels. The amount of charge delivered to individual electrodes is a function of stimulation amplitude and pulse width. Hence, a lowering the compliance voltage (and, in effect, the stimulation amplitude) may necessitate a widening of the pulse width to achieve comfortable loudness sensation. Widened pulse widths may adversely affect (i.e., decrease) the stimulation rate (i.e., the number of stimulation pulses that may be applied per given time unit). This, in turn, may lead to poor or unacceptable sound quality for some cochlear implant patients.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for maximizing loudness sensation produced by electrical stimulation in a cochlear implant patient are described herein. As used herein, "loudness sensation" refers to a loudness level perceived by a cochlear implant patient in response to electrical stimulation generated and applied by a cochlear implant system.

In some examples, a sound processor may process an audio signal presented to a cochlear implant patient and direct a cochlear implant to apply electrical stimulation representative of the audio signal to the cochlear implant patient by 1) directing the cochlear implant to concurrently apply a first biphasic stimulation pulse by way of a first electrode and a second biphasic stimulation pulse by way of a second electrode during a first time slot, and 2) directing the cochlear implant to concurrently apply a third biphasic stimulation pulse by way of the second electrode and a fourth biphasic stimulation pulse by way of a third electrode during a second time slot that immediately follows the first time slot. As will be described in more detail below, the third and fourth biphasic stimulation pulses are flipped in phase compared to the first and second biphasic stimulation pulses.

To illustrate, cathode-anode biphasic stimulation pulses (i.e., stimulation pulses that have negative first phases followed by positive second phases) may be applied by way of a first electrode and a second electrode during a first time slot included in a stimulation frame. Anode-cathode biphasic stimulation pulses (i.e., stimulation pulses that have positive first phases followed by negative second phases) may subsequently be applied by way of the second electrode and a third electrode during a second time slot that immediately follows the first time slot. In this example, the cathode-anode biphasic stimulation pulse and the anode-cathode biphasic stimulation pulse applied sequentially by way of the second electrode combine to effectively create a triphasic stimulation pulse that has a relatively short negative phase followed by a relatively long positive phase (i.e., a positive phase that is double in width compared to the relatively short negative phase) followed by another relatively short negative phase.

By applying back-to-back stimulation pulses that are flipped in phase relative to one another by way of the same electrode in this manner, the systems and methods described herein may result in relatively long middle phases being applied by way of each electrode, thereby maximizing the loudness sensation generated by the stimulation pulses applied by way of the electrodes without negatively impacting the stimulation rate. For example, if the systems and methods described herein are applied to all of the electrodes in a particular electrode array included in a cochlear implant patient, the systems and methods described herein may significantly increase (e.g., by twenty percent or more) the loudness sensation without reducing the stimulation rate compared to conventional sound processing schemes where phase flipped stimulation pulses are not used. This may facilitate reduced compliance voltages, increased battery life, improved performance, and/or other benefits compared to conventional sound processing schemes.

Figure 1:
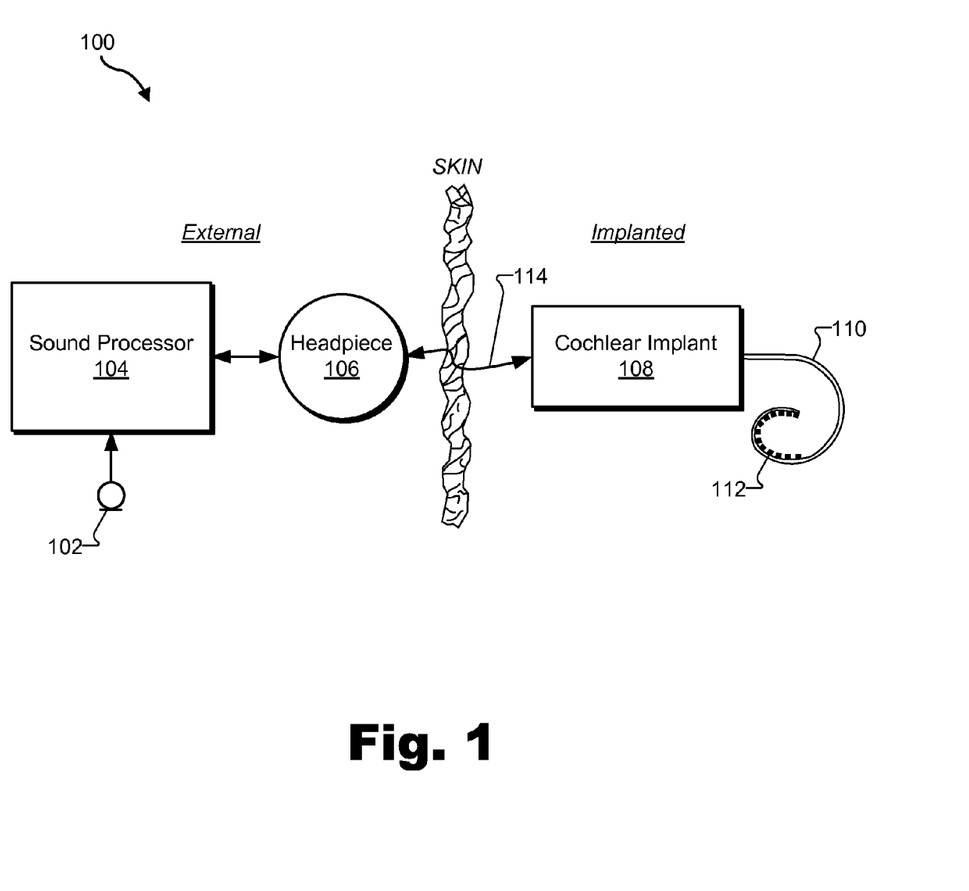
FIG. 1 illustrates an exemplary cochlear implant system according to principles described herein.

FIG. 1 illustrates an exemplary cochlear implant system 100. As shown, cochlear implant system 100 may include various components configured to be located external to a patient including, but not limited to, a microphone 102, a sound processor 104, and a headpiece 106. Cochlear implant system 100 may further include various components configured to be implanted within the patient including, but not limited to, a cochlear implant 108 and a lead 110 (also referred to as an electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a "T-Mic" or the like that is configured to be placed within the concha of the ear near the entrance to the ear canal. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
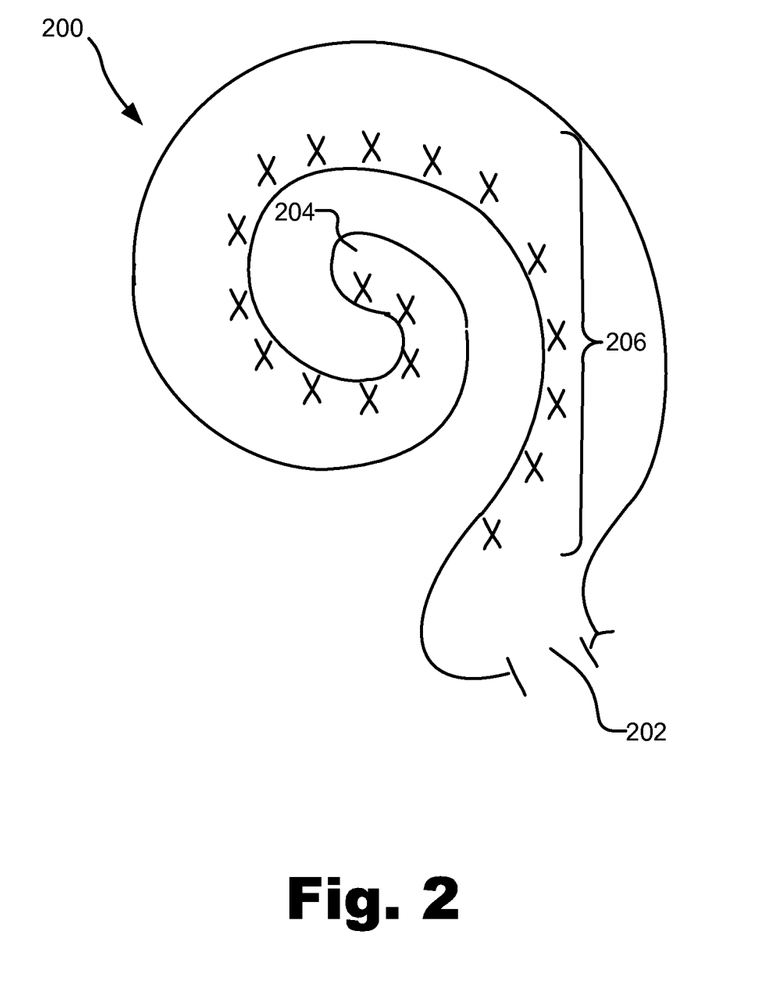
FIG. 2 illustrates a schematic structure of the human cochlea according to principles described herein.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
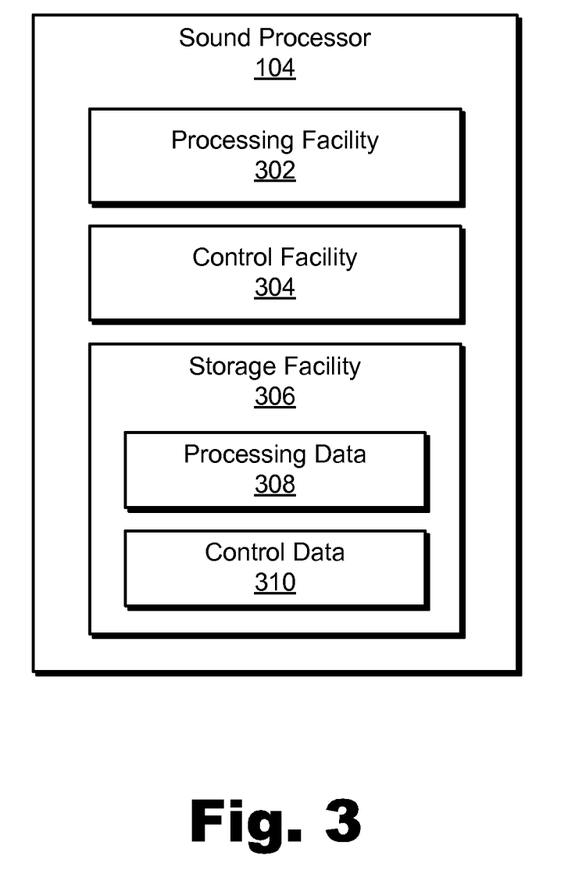
FIG. 3 illustrates exemplary components of a sound processor according to principles described herein.

FIG. 3 illustrates exemplary components of sound processor 104. It will be recognized that the components shown in FIG. 3 are merely representative of the many different components that may be included in sound processor 104 and that sound processor 104 may include additional or alternative components as may serve a particular implementation.

As shown in FIG. 3, sound processor 104 may include a processing facility 302, a control facility 304, and a storage facility 306, which may be in communication with one another using any suitable communication technologies. One or more of facilities 302-306 may include a computing device or processor configured to perform one or more of the functions described herein. Facilities 302-306 will now be described in more detail.

Processing facility 302 may be configured to process an audio signal presented to a cochlear implant patient (i.e., an audio signal detected by microphone 102). For example, processing facility 302 may perform one or more pre-processing operations, spectral analysis operations, noise reduction operations, mapping operations, and/or any other types of signal processing operations on a detected audio signal as may serve a particular application. In some examples, as will be described below, processing facility 302 may process an audio signal by identifying a frequency range associated with a dominant feature of the audio signal (e.g., a spectral peak included in the audio signal, such as a formant of speech or music).

Control facility 304 may be configured to direct cochlear implant 108 to apply electrical stimulation representative of the audio signal to the cochlear implant patient. This may be performed in any suitable manner. For example, control facility 304 may generate and transmit one or more control parameters to cochlear implant 108. The one or more control parameters may define one or more characteristics of the electrical stimulation applied by cochlear implant 108.

In some examples, control facility 304 may be configured to direct cochlear implant 108 to apply electrical stimulation representative of the audio signal in accordance with a current steering strategy. Current steering may include concurrently stimulating multiple (e.g., two) electrodes that surround, but that are not directly associated with, a particular stimulation site in order to steer current to (and thereby apply electrical stimulation to) the stimulation site.

Figure 4:
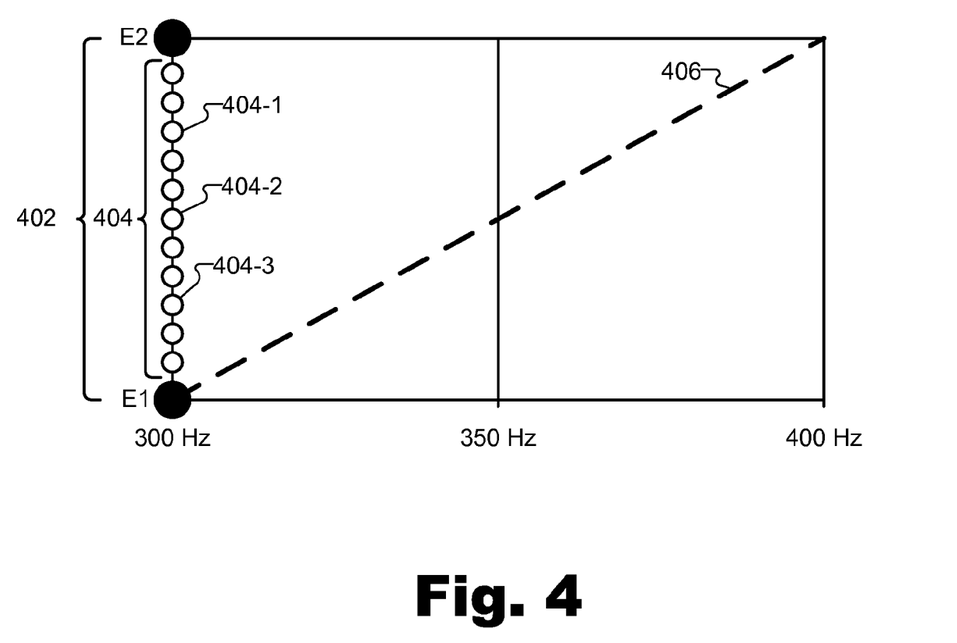
FIG. 4 shows an exemplary channel defined by first and second physical electrodes according to principles described herein.

To illustrate current steering, FIG. 4 shows an exemplary channel 402 defined by first and second physical electrodes E1 and E2. Channel 402 may be associated with any frequency band as may serve a particular implementation. In the example of FIG. 4, channel 402 is associated with a frequency band having a minimum frequency of 300 Hz and a maximum frequency of 400 Hz. It will be recognized that the current steering range may alternatively be centered about any other point within the channel as may serve a particular implementation.

As shown, channel 402 may be conceptualized as having a plurality of virtual electrodes 404 (e.g., virtual electrodes 404-1, 404-2, and 404-3) disposed in between physical electrodes E1 and E2. Each virtual electrode 404 represents a particular location along an electrode lead (e.g., lead 110) and in between physical electrodes E1 and E2. For example, virtual electrode 404-2 represents a midpoint of channel 402 about which a current steering range associated with channel 402 is centered.

Channel 402 may have any current steering range associated therewith. The current steering range defines a range of current steering that may be used within a channel. For example, the current steering range 402 associated with channel 402 may include any number of the virtual electrodes 404 included in channel 402, and, in some instances, may also include physical electrodes E1 and E2.

Line 406 represents an exemplary frequency-to-electrode mapping in cases where the current steering range includes all virtual electrodes 404 as well as physical electrodes E1 and E2. As shown by line 406, 300 Hz is mapped to physical electrode E1, 400 Hz is mapped to physical electrode E2, and each frequency in between 300 Hz and 400 Hz is mapped to virtual electrodes 404.

Using the frequency-to-electrode mapping represented by line 406, control facility 304 may direct cochlear implant 108 to apply electrical stimulation representative of acoustic content having a frequency included within the range of frequencies shown in FIG. 4 by directing cochlear implant 108 to concurrently apply electrical stimulation (e.g., biphasic stimulation pulses) by way of electrodes E1 and E2. For example, if acoustic content included in an audio signal presented to the cochlear implant patient has a frequency of 350 Hz, control facility 304 may direct cochlear implant 108 to concurrently apply biphasic stimulation pulses of equal amplitude by way of E1 and E2 to effectively stimulate virtual electrode 404-2.

It will be assumed in the examples provided herein that current steering is achieved by concurrently stimulating two electrodes during a particular time slot of a stimulation frame. However, it will be recognized that more than two electrodes may be concurrently stimulated during a particular time slot as may serve a particular implementation.

In some examples, control facility 304 may direct cochlear implant 108 to apply electrical stimulation representative of the audio signal to the cochlear implant patient by directing cochlear implant 108 to apply back-to-back stimulation pulses that are flipped in phase relative to one another by way of the same electrode. As described above, this may maximize the loudness sensation generated by the stimulation pulses.

Figure 5:
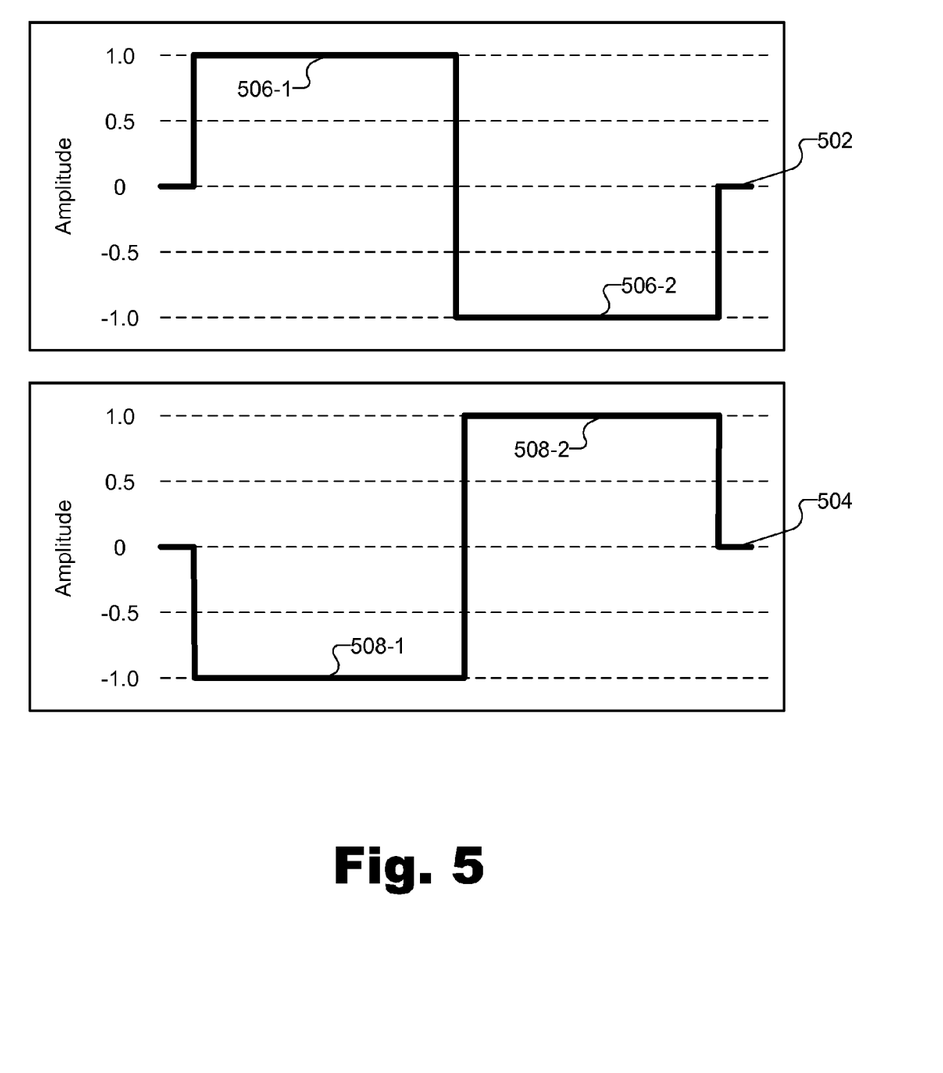
FIG. 5 illustrates exemplary biphasic stimulation pulses that are flipped in phase relative to one another according to principles described herein.

FIG. 5 illustrates exemplary biphasic stimulation pulses 502 and 504 that are flipped in phase relative to one another. Biphasic stimulation pulse 502 may be referred to as an "anode-cathode biphasic stimulation pulse" because it includes a positive phase 506-1 (i.e., a phase having an amplitude that is positive) followed by a negative phase 506-2 (i.e., a phase having an amplitude that is negative). Conversely, biphasic stimulation pulse 504 includes a negative phase 508-1 followed by a positive phase 508-2. Hence, biphasic stimulation pulse 504 may be referred to as a "cathode-anode biphasic stimulation pulse".

Figure 6:
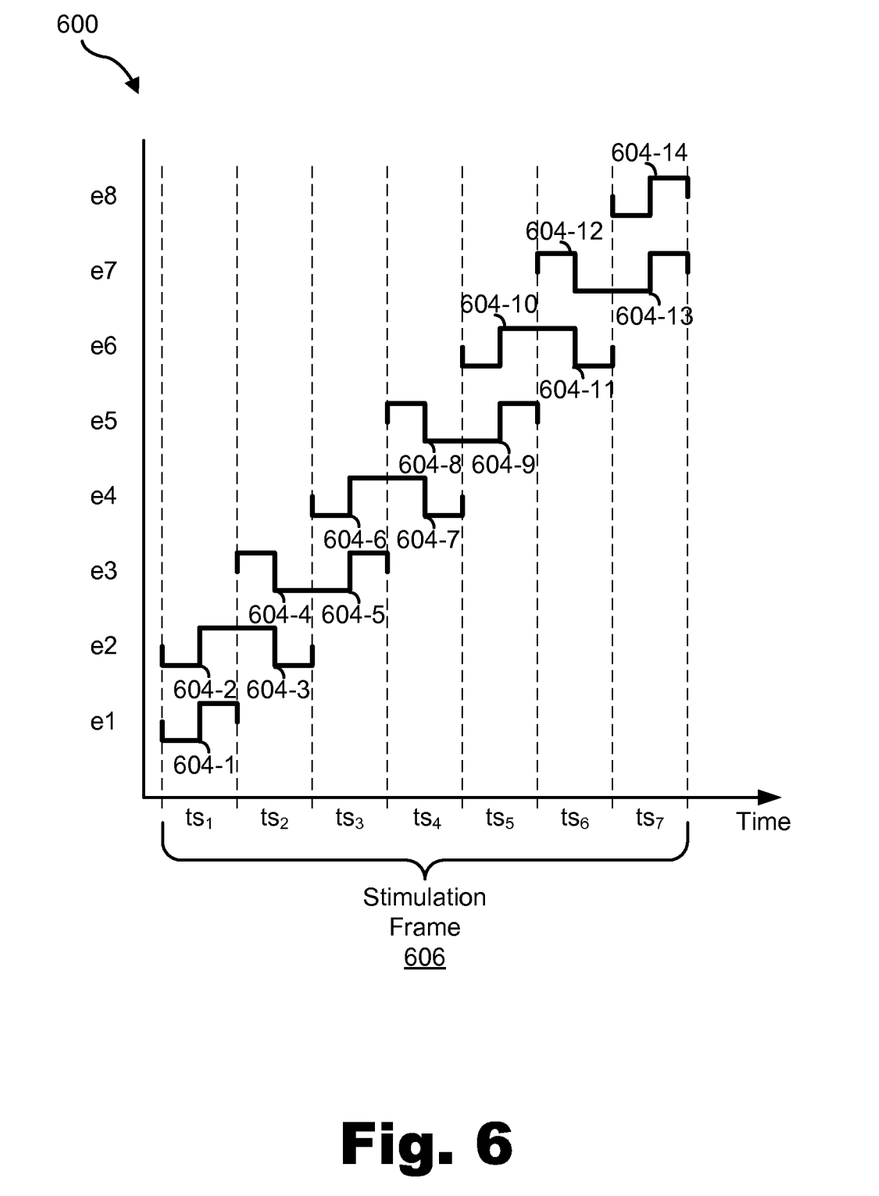
FIG. 6 illustrates an exemplary stimulation strategy that may be used in accordance with the systems and methods described herein.

FIG. 6 illustrates an exemplary flipped phase stimulation strategy 600 that may be used in accordance with the systems and methods described herein. As shown, a plurality of biphasic stimulation pulses 604 (e.g., 604-1 through 604-14) may be applied by way of a plurality of electrodes e1 through e8 during a stimulation frame 606 that includes a plurality of time slots $ts_1$ through $ts_7$. While eight electrodes are shown in the example of FIG. 6, it will be recognized that any other number of electrodes (e.g., sixteen) may be included in the electrode array to which flipped phase stimulation strategy 600 is applied.

In the example of FIG. 6, two biphasic stimulation pulses 604 are applied by way of two electrodes (e.g., two electrodes that make up a channel) during each time slot included in stimulation frame 606. In this manner, the two biphasic stimulation pulses 604 may combine to steer current to any desired virtual electrode located in between the two electrodes. While each biphasic stimulation pulse 604 shown in FIG. 6 has the same amplitude and pulse width, it will be recognized that biphasic stimulation pulses 604 may differ in amplitude and/or pulse width as may serve a particular implementation.

As shown, flipped phase stimulation strategy 600 may include back-to-back biphasic stimulation pulses that are flipped in phase compared to one another being applied by way of the same electrode during sequential time slots. To illustrate, FIG. 6 shows that control facility 304 may direct cochlear implant 108 to concurrently apply a first biphasic stimulation pulse 604-1 by way of a first electrode e1 and a second biphasic stimulation pulse 604-2 by way of a electrode e2 during a first time slot $ts_1$. Control facility 304 may then direct cochlear implant 108 to concurrently apply a third biphasic stimulation pulse 604-3 by way of the second electrode e2 and a fourth biphasic stimulation pulse 604-4 by way of a third electrode e3 during a second time slot $ts_2$ that immediately follows the first time slot $ts_1$.

As shown, the third and fourth biphasic stimulation pulses 604-3 and 604-4 are flipped in phase compared to the first and second biphasic stimulation pulses 604-1 and 604-2. In the particular example of FIG. 6, the first and second biphasic stimulation pulses 604-1 and 604-2 are cathode-anode biphasic stimulation pulses and the third and fourth biphasic stimulation pulses 604-3 and 604-4 are anode-cathode biphasic stimulation pulses. It will be recognized that this is merely exemplary, and that the first and second biphasic stimulation pulses 604-1 and 604-2 may alternatively be anode-cathode biphasic stimulation pulses and the third and fourth biphasic stimulation pulses 604-3 and 604-4 may alternatively be cathode-anode biphasic stimulation pulses.

As shown, the second phase of biphasic stimulation pulse 604-2 and the first phase of biphasic stimulation pulse 604-3 applied by way of electrode e2 advantageously combine to create a relatively long middle phase (i.e., a positive phase that is twice as long as the first phase of biphasic stimulation pulse 604-2 and the last phase of biphasic stimulation pulse 604-3). As described above, this may increase a loudness level of the audio signal as perceived by the cochlear implant patient (i.e., a loudness sensation) compared to a loudness level of the audio signal that results when biphasic stimulation pulse 604-3 is not flipped in phase compared to biphasic stimulation pulse 604-2.

In some examples, processing facility 302 may set an amplitude of any of biphasic stimulation pulses 604 in accordance with a most comfortable current level (i.e., an "M level") associated with the cochlear implant patient. For example, because the loudness sensation produced by the biphasic stimulation pulses 604 is maximized, processing facility 302 may lower the amplitude of biphasic stimulation pulses 604 and still achieve a suitable M level associated with the cochlear implant patient.

As shown, the phases of the biphasic stimulation pulses 604 may be flipped during each sequential time slot included in stimulation frame 606. In this manner, power consumption across the entire electrode array may be minimized. Alternatively, phases may be flipped during only select time slots included in stimulation frame 606. In this manner, a particular feature (e.g., a dominant feature) of an audio signal may be more dominantly represented to a cochlear implant patient than other portions of the audio signal.

Figure 7:
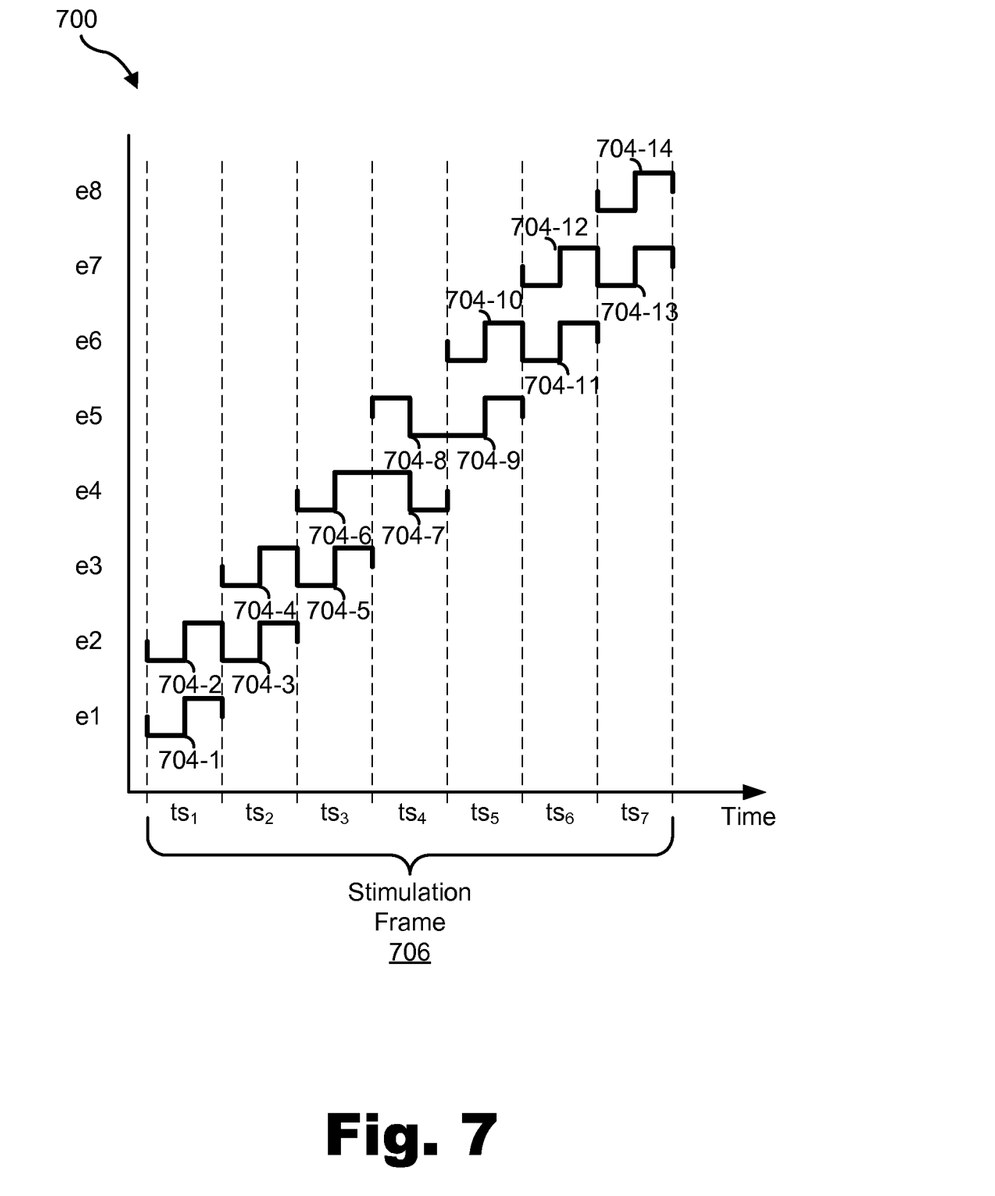
FIG. 7 illustrates another exemplary stimulation strategy that may be used in accordance with the systems and methods described herein according to principles described herein.

To illustrate, FIG. 7 illustrates an exemplary stimulation strategy 700 that may be used in accordance with the systems and methods described herein. As shown, a plurality of biphasic stimulation pulses 704 (e.g., 704-1 through 704-14) may be applied by way of a plurality of electrodes e1 through e8 during a stimulation frame 706 that includes a plurality of time slots $ts_1$ through $ts_7$. In the example of FIG. 7, two biphasic stimulation pulses 704 are applied by way of two electrodes (e.g., two electrodes that make up a channel) during each time slot included in stimulation frame 706. In this manner, the two biphasic stimulation pulses 704 may combine to steer current to any desired virtual electrode located in between the two electrodes. While each biphasic stimulation pulse 704 shown in FIG. 7 has the same amplitude and pulse width, it will be recognized that biphasic stimulation pulses 704 may differ in amplitude and/or pulse width as may serve a particular implementation.

In the example of FIG. 7, back-to-back biphasic stimulation pulses that are flipped in phase compared to one another are only applied by way of a subset of electrodes e1-e8 (i.e., by way of electrodes e4 and e5). The remaining biphasic stimulation pulses applied by way of the other electrodes (i.e., electrodes e1-e3 and e6-e8) are not flipped in phase compared to one another. In this manner, a dominant feature of an audio signal may be more effectively conveyed to the cochlear implant patient.

To illustrate, processing facility 302 may identify a frequency range associated with a dominant feature of an audio signal presented to a patient. In the example of FIG. 7, the identified frequency range is associated with the channels made up by electrodes e3 and e4 and electrodes e4 and e5. Based on this information, control facility 304 may direct cochlear implant 108 to concurrently apply a first biphasic stimulation pulse 704-5 by way of electrode e3 and a second biphasic stimulation pulse 704-6 by way of electrode e4 during time slot $ts_3$. Control facility 304 may then direct cochlear implant 108 to concurrently apply a third biphasic stimulation pulse 704-7 by way of electrode e4 and a fourth biphasic stimulation pulse 704-8 by way of electrode e5 during time slot $ts_4$.

As shown, third and fourth biphasic stimulation pulses 704-7 and 704-8 are flipped in phase compared to first and second biphasic stimulation pulses 704-5 and 704-6 and compared to a remaining number of biphasic stimulation pulses (i.e., biphasic stimulation pulses 704-1 through 704-4 and 704-9 through 704-14) applied by way of electrodes not associated with the identified frequency range. In this manner, the biphasic stimulation pulses applied by way of electrodes e4 and e5 (i.e., biphasic stimulation pulses 704-6 and 704-7 and biphasic stimulation pulses 704-8 and 704-9, respectively) may maximize loudness sensation for the dominant feature of the audio signal compared to other portions of the audio signal represented by the other biphasic stimulation pulses (i.e., biphasic stimulation pulses 704-1 through 704-4 and 704-9 through 704-14).

Returning to FIG. 3, storage facility 306 may be configured to maintain processing data 308 generated and/or used by processing facility 302 and/or control data 310 (e.g., data representative of one or more control parameters) generated and/or used by control facility 304. It will be recognized that storage facility 306 may maintain additional or alternative data as may serve a particular implementation.

Figure 8:
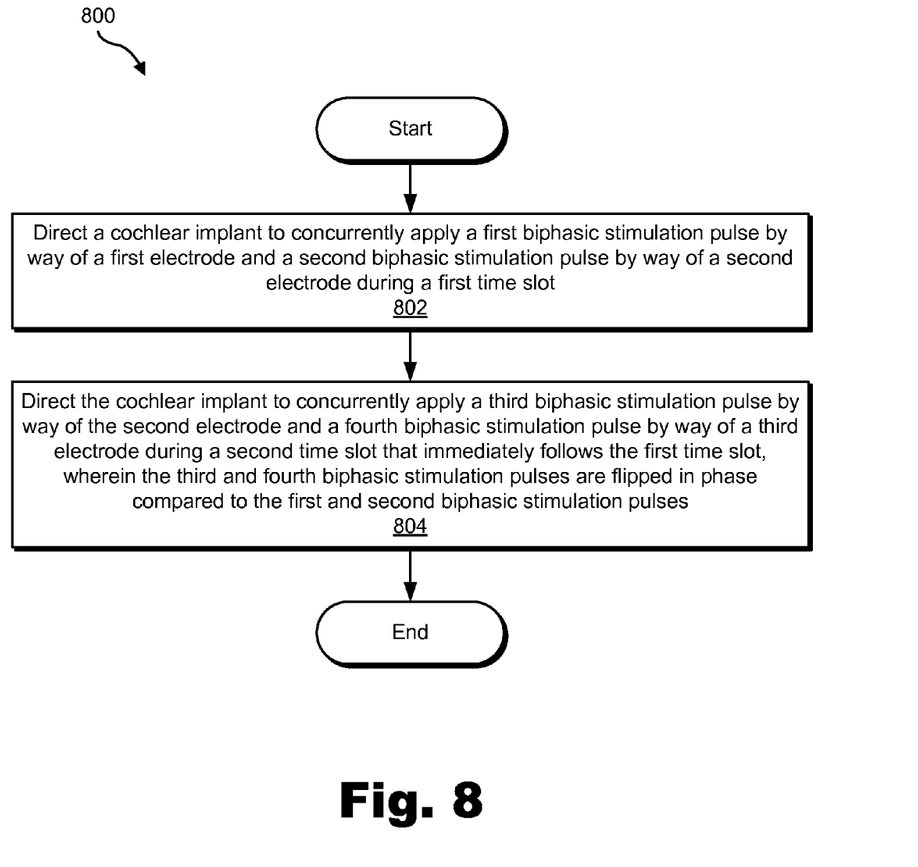
FIG. 8 illustrates an exemplary method of maximizing loudness sensation in a cochlear implant patient according to principles described herein.

FIG. 8 illustrates an exemplary method 800 of maximizing loudness sensation in a cochlear implant patient. While FIG. 8 illustrates exemplary steps according to one embodiment, other embodiments may omit, add to, reorder, and/or modify any of the steps shown in FIG. 8. One or more of the steps shown in FIG. 8 may be performed by sound processor 104 and/or any implementation thereof.

In step 802, a sound processor directs a cochlear implant to concurrently apply a first biphasic stimulation pulse by way of a first electrode and a second biphasic stimulation pulse by way of a second electrode during a first time slot. Step 802 may be performed in any of the ways described herein.

In step 804, the sound processor directs the cochlear implant to concurrently apply a third biphasic stimulation pulse by way of the second electrode and a fourth biphasic stimulation pulse by way of a third electrode during a second time slot that immediately follows the first time slot. As described above, the third and fourth biphasic stimulation pulses are flipped in phase compared to the first and second biphasic stimulation pulses. Step 804 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:

directing, by a sound processor, a cochlear implant to concurrently apply a first biphasic stimulation pulse by way of a first electrode and a second biphasic stimulation pulse by way of a second electrode during a first time slot; and directing, by the sound processor, the cochlear implant to concurrently apply a third biphasic stimulation pulse by way of the second electrode and a fourth biphasic stimulation pulse by way of a third electrode during a second time slot that immediately follows the first time slot;

wherein the third and fourth biphasic stimulation pulses are flipped in phase compared to the first and second biphasic stimulation pulses.

2. The method of claim 1, further comprising:

identifying, by the sound processor, a frequency range associated with a dominant feature of the audio signal;

wherein the first, second, and third electrodes are associated with the identified frequency range; and wherein the first, second, third, and fourth biphasic stimulation pulses are configured to convey the dominant feature of the audio signal to the patient.

3. The method of claim 1, wherein the application of the second biphasic stimulation pulse during the first time slot and the third biphasic stimulation pulse during the second time slot results is configured to increase a loudness level of the audio signal as perceived by the cochlear implant patient compared to a loudness level of the audio signal that results when the third and fourth biphasic stimulation pulses are not flipped in phase compared to the first and second biphasic stimulation pulses.

4. The method of claim 1, wherein the first and second biphasic stimulation pulses are cathode-anode biphasic stimulation pulses and the third and fourth biphasic stimulation pulses are anode-cathode biphasic stimulation pulses.

5. The method of claim 1, wherein the first and second biphasic stimulation pulses are anode-cathode biphasic stimulation pulses and the third and fourth biphasic stimulation pulses are cathode-anode biphasic stimulation pulses.

6. The method of claim 1, further comprising:

directing, by the sound processor, the cochlear implant to concurrently apply a fifth biphasic stimulation pulse by way of the third electrode and a sixth biphasic stimulation pulse by way of a fourth electrode during a third time slot that immediately follows the second time slot;

wherein the fifth and sixth biphasic stimulation pulses are flipped in phase compared to the third and fourth biphasic stimulation pulses.

7. A system comprising:

a processing facility configured to process an audio signal presented to a cochlear implant patient; and a control facility communicatively coupled to the processing facility and configured to direct a cochlear implant to apply electrical stimulation representative of the audio signal to the cochlear implant patient by directing the cochlear implant to concurrently apply a first biphasic stimulation pulse by way of a first electrode and a second biphasic stimulation pulse by way of a second electrode during a first time slot, and directing the cochlear implant to concurrently apply a third biphasic stimulation pulse by way of the second electrode and a fourth biphasic stimulation pulse by way of a third electrode during a second time slot that immediately follows the first time slot;

wherein the third and fourth biphasic stimulation pulses are flipped in phase compared to the first and second biphasic stimulation pulses.

8. The system of claim 7, wherein:

the processing facility is configured to process the audio signal by identifying a frequency range associated with a dominant feature of the audio signal;

wherein the first, second, and third electrodes are associated with the identified frequency range; and wherein the first, second, third, and fourth biphasic stimulation pulses are configured to convey the dominant feature of the audio signal to the patient.

9. The system of claim 8, wherein the control facility is further configured to direct the cochlear implant to apply the electrical stimulation representative of the audio signal to the cochlear implant patient by directing the cochlear implant to apply a plurality of additional biphasic stimulation pulses by way of a plurality of additional electrodes not associated with the identified frequency range during a plurality of additional time slots;

wherein the plurality of additional biphasic stimulation pulses are not flipped in phase compared to the first and second biphasic stimulation pulses.

10. The system of claim 7, wherein the processing facility is configured to set the amplitude of the first, second, third, and fourth biphasic stimulation pulses in accordance with a most comfortable current level associated with the cochlear implant patient.

11. The system of claim 7, wherein the application of the second biphasic stimulation pulse during the first time slot and the third biphasic stimulation pulse during the second time slot is configured to increase a loudness level of the audio signal as perceived by the cochlear implant patient compared to a loudness level of the audio signal that results when the third and fourth biphasic stimulation pulses are not flipped in phase compared to the first and second biphasic stimulation pulses.

12. The system of claim 7, wherein the first and second biphasic stimulation pulses and the third and fourth biphasic stimulation pulses are applied in accordance with a current steering strategy.

13. The system of claim 7, wherein the first and second biphasic stimulation pulses are cathode-anode biphasic stimulation pulses and the third and fourth biphasic stimulation pulses are anode-cathode biphasic stimulation pulses.

14. The system of claim 7, wherein the first and second biphasic stimulation pulses are anode-cathode biphasic stimulation pulses and the third and fourth biphasic stimulation pulses are cathode-anode biphasic stimulation pulses.

15. The system of claim 7, wherein the control facility is further configured to direct the cochlear implant to apply the electrical stimulation representative of the audio signal to the cochlear implant patient by directing the cochlear implant to concurrently apply a fifth biphasic stimulation pulse by way of the third electrode and a sixth biphasic stimulation pulse by way of a fourth electrode during a third time slot that immediately follows the second time slot;

wherein the fifth and sixth biphasic stimulation pulses are flipped in phase compared to the third and fourth biphasic stimulation pulses.

16. The system of claim 7, wherein the audio signal comprises speech.

17. A system comprising:

a processing facility configured to identify a frequency range associated with a dominant feature of an audio signal presented to a patient; and a control facility communicatively coupled to the processing facility and configured to direct a cochlear implant to apply electrical stimulation representative of the audio signal to the cochlear implant patient by directing the cochlear implant to concurrently apply a first biphasic stimulation pulse by way of a first electrode associated with the identified frequency range and a second biphasic stimulation pulse by way of a second electrode associated with the identified frequency range during a first time slot included in a stimulation frame, directing the cochlear implant to concurrently apply a third biphasic stimulation pulse by way of the second electrode and a fourth biphasic stimulation pulse by way of a third electrode associated with the identified frequency range during a second time slot included in the stimulation frame and that immediately follows the first time slot, and directing the cochlear implant to apply a plurality of additional biphasic stimulation pulses by way of a plurality of additional electrodes not associated with the identified frequency range during a plurality of additional time slots included in the stimulation frame;

wherein the third and fourth biphasic stimulation pulses are flipped in phase compared to the first biphasic stimulation pulse, the second biphasic stimulation pulse, and the plurality of additional biphasic stimulation pulses; and wherein the first, second, third, and fourth biphasic stimulation pulses are configured to convey the dominant feature of the audio signal to the patient.

18. The system of claim 17, wherein the first and second biphasic stimulation pulses and the plurality of additional biphasic stimulation pulses are cathode-anode biphasic stimulation pulses and the third and fourth biphasic stimulation pulses are anode-cathode biphasic stimulation pulses.

19. The system of claim 17, wherein the first and second biphasic stimulation pulses and the plurality of additional biphasic stimulation pulses are anode-cathode biphasic stimulation pulses and the third and fourth biphasic stimulation pulses are cathode-anode biphasic stimulation pulses.

20. The system of claim 17, wherein the audio signal comprises speech and the dominant feature comprises a formant of the speech.

* * * * *